(12) United States Patent
Baker et al.

(10) Patent No.: US 9,700,308 B2
(45) Date of Patent: *Jul. 11, 2017

(54) TISSUE FIXATION DEVICES AND ASSEMBLIES FOR DEPLOYING THE SAME

(71) Applicant: ENDOGASTRIC SOLUTIONS, INC., Redmond, WA (US)

(72) Inventors: Steve G. Baker, Redmond, WA (US); Brett J. Carter, Monroe, WA (US)

(73) Assignee: ENDOGASTRIC SOLUTIONS, INC., Redmond, WA (US)

( * ) Notice: Subject to any disclaimer, the term of this patent is extended or adjusted under 35 U.S.C. 154(b) by 194 days.

This patent is subject to a terminal disclaimer.

(21) Appl. No.: 14/558,837

(22) Filed: Dec. 3, 2014

(65) Prior Publication Data

US 2015/0088170 A1    Mar. 26, 2015

Related U.S. Application Data

(60) Division of application No. 12/590,203, filed on Nov. 4, 2009, now Pat. No. 8,911,473, which is a
(Continued)

(51) Int. Cl.
*A61B 17/04*     (2006.01)
*A61B 17/08*     (2006.01)
(Continued)

(52) U.S. Cl.
CPC ...... *A61B 17/0644* (2013.01); *A61B 17/0401* (2013.01); *A61B 17/064* (2013.01);
(Continued)

(58) Field of Classification Search
CPC ............ A61B 17/0644; A61B 17/0401; A61B 17/064; A61B 17/068; A61B 17/10;
(Continued)

(56) References Cited

U.S. PATENT DOCUMENTS 2,753,870 A    7/1956  Muffly
3,875,928 A    4/1975  Angelchik
(Continued)

FOREIGN PATENT DOCUMENTS

EP    252607 A2    9/1992
WO    9922649 A2   5/1999
(Continued)

OTHER PUBLICATIONS

The gastroesophageal flap valve: in vitro and in vivo observations; Lucius D. Hill et al.; Gastrointestinal Endoscopy; vol. 44, No. 5, 1996; pp. 541-547; abstract.
(Continued)

*Primary Examiner* — Julian W Woo
(74) *Attorney, Agent, or Firm* — Fulwider Patton LLP

(57) ABSTRACT

Tissue fasteners carried on a tissue piercing deployment wire fasten tissue layers of a mammalian body together include a first member, a second member, and a connecting member extending between the first and second members. One of the first and second members has an elongated slot permitting fastener deployment while avoiding excessive tissue compression.

16 Claims, 9 Drawing Sheets

Related U.S. Application Data continuation of application No. 10/949,737, filed on Sep. 23, 2004, now Pat. No. 7,632,287, which is a continuation-in-part of application No. 10/783,717, filed on Feb. 20, 2004, now abandoned.

(51) Int. Cl.
  *A61B 17/064* (2006.01)
  *A61B 17/068* (2006.01)
  *A61B 17/10* (2006.01)
  *A61B 17/128* (2006.01)
  *A61B 17/00* (2006.01)

(52) U.S. Cl.
  CPC ............ *A61B 17/068* (2013.01); *A61B 17/10* (2013.01); *A61B 17/1285* (2013.01); *A61B 17/0469* (2013.01); *A61B 2017/00827* (2013.01); *A61B 2017/0409* (2013.01); *A61B 2017/0414* (2013.01); *A61B 2017/0419* (2013.01)

(58) Field of Classification Search
  CPC ............ A61B 17/1285; A61B 17/0469; A61B 2017/00827; A61B 2017/0409; A61B 2017/0414; A61B 2017/0419
  See application file for complete search history.

(56) References Cited

U.S. PATENT DOCUMENTS

| | | | |
|---|---|---|---|
| 3,976,079 A * | 8/1976 | Samuels | A61B 17/0466 24/115 M |
| 4,006,747 A | 2/1977 | Kronenthal | |
| 4,271,828 A | 6/1981 | Angelchik | |
| 4,576,772 A | 3/1986 | Carpenter et al. | |
| 4,595,007 A | 6/1986 | Mericle | |
| 4,669,473 A | 6/1987 | Richards et al. | |
| 4,696,300 A | 9/1987 | Anderson | |
| 4,846,836 A | 7/1989 | Reich | |
| 4,895,148 A | 1/1990 | Bays et al. | |
| 4,921,479 A | 5/1990 | Grayzel | |
| 5,006,106 A | 4/1991 | Angelchik et al. | |
| 5,041,129 A | 8/1991 | Hayhurst et al. | |
| 5,080,543 A | 1/1992 | Murphy | |
| 5,088,979 A | 2/1992 | Filipi et al. | |
| 5,254,126 A | 10/1993 | Filipi et al. | |
| 5,269,809 A * | 12/1993 | Hayhurst | A61B 17/0401 606/151 |
| 5,314,473 A | 5/1994 | Godin | |
| 5,403,326 A | 4/1995 | Harrison et al. | |
| 5,411,508 A | 5/1995 | Bessler et al. | |
| 5,411,520 A | 5/1995 | Nash et al. | |
| 5,549,621 A | 8/1996 | Bessler et al. | |
| 5,571,074 A | 11/1996 | Buckman et al. | |
| 5,571,116 A | 11/1996 | Bolanos et al. | |
| 5,626,614 A | 5/1997 | Hart | |
| 5,676,674 A | 10/1997 | Bolanos et al. | |
| 5,713,903 A | 2/1998 | Sander et al. | |
| 5,759,151 A | 6/1998 | Sturges | |
| 5,810,882 A | 9/1998 | Bolduc et al. | |
| 5,814,054 A | 9/1998 | Kortenbach et al. | |
| 5,861,036 A | 1/1999 | Godin | |
| 5,879,372 A | 3/1999 | Bartlett et al. | |
| 5,887,594 A | 3/1999 | LoCicero | |
| 5,897,562 A | 4/1999 | Bolanos et al. | |
| 5,938,668 A | 8/1999 | Scirica et al. | |
| 6,086,600 A | 7/2000 | Kortenbach | |
| 6,098,629 A | 8/2000 | Johnson et al. | |
| 6,113,609 A | 9/2000 | Adams | |
| 6,113,611 A | 9/2000 | Allen et al. | |
| 6,142,957 A | 11/2000 | Diamond et al. | |
| 6,254,642 B1 | 7/2001 | Taylor | |
| 6,264,700 B1 | 7/2001 | Kilcoyne et al. | |
| 6,302,311 B1 | 10/2001 | Adams et al. | |
| 6,302,917 B1 | 10/2001 | Dua et al. | |
| 6,312,437 B1 | 11/2001 | Kortenbach | |
| 6,315,789 B1 | 11/2001 | Cragg | |
| 6,419,669 B1 | 7/2002 | Frazier et al. | |
| 6,428,548 B1 | 8/2002 | Durgin et al. | |
| 6,447,524 B1 | 9/2002 | Knodel et al. | |
| 6,743,239 B1 | 6/2004 | Kuehn et al. | |
| 6,773,440 B2 | 8/2004 | Gannoe et al. | |
| 6,773,441 B1 | 8/2004 | Laufer et al. | |
| 6,790,214 B2 | 9/2004 | Kraemer et al. | |
| 6,835,200 B2 | 12/2004 | Laufer et al. | |
| 6,916,332 B2 | 7/2005 | Adams | |
| 6,921,361 B2 | 7/2005 | Suzuki et al. | |
| 7,022,118 B2 | 4/2006 | Ariura et al. | |
| 7,037,344 B2 | 5/2006 | Kagan et al. | |
| 7,074,229 B2 | 7/2006 | Adams et al. | |
| 7,083,630 B2 | 8/2006 | DeVries et al. | |
| 7,220,266 B2 | 5/2007 | Gambale | |
| 7,347,863 B2 | 3/2008 | Rothe et al. | |
| 7,618,426 B2 | 11/2009 | Ewers et al. | |
| 7,632,287 B2 * | 12/2009 | Baker | A61B 17/0401 606/151 |
| 7,678,123 B2 | 3/2010 | Chanduszko | |
| 7,713,277 B2 | 5/2010 | Laufer et al. | |
| 7,766,939 B2 * | 8/2010 | Yeung | A61B 17/0401 606/232 |
| 7,776,057 B2 | 8/2010 | Laufer et al. | |
| 7,850,704 B2 | 12/2010 | Burnett et al. | |
| 7,857,184 B2 | 12/2010 | Viola | |
| 7,857,823 B2 | 12/2010 | Laufer et al. | |
| 7,866,526 B2 | 1/2011 | Green et al. | |
| 7,942,887 B2 | 5/2011 | Kraemer et al. | |
| 7,951,157 B2 | 5/2011 | Gambale | |
| 7,954,687 B2 | 6/2011 | Zemlok et al. | |
| 7,955,340 B2 | 6/2011 | Michlitsch et al. | |
| 8,057,494 B2 | 11/2011 | Laufer et al. | |
| 8,252,009 B2 | 8/2012 | Weller et al. | |
| 8,277,468 B2 | 10/2012 | Laufer et al. | |
| 8,308,765 B2 | 11/2012 | Saadat et al. | |
| 8,343,175 B2 | 1/2013 | Ewers et al. | |
| 8,574,243 B2 | 11/2013 | Saadat et al. | |
| 8,911,473 B2 * | 12/2014 | Baker | A61B 17/0401 606/151 |
| 2002/0022853 A1 | 2/2002 | Swanson et al. | |
| 2002/0035370 A1 | 3/2002 | Kortenbach | |
| 2002/0040226 A1 | 4/2002 | Laufer et al. | |
| 2002/0055772 A1 | 5/2002 | McGuckin, Jr. et al. | |
| 2002/0072761 A1 | 6/2002 | Abrams et al. | |
| 2002/0078967 A1 | 6/2002 | Sixto, Jr. et al. | |
| 2002/0082621 A1 | 6/2002 | Schurr et al. | |
| 2002/0143349 A1 | 10/2002 | Gifford, III et al. | |
| 2002/0183765 A1 | 12/2002 | Adams | |
| 2002/0198541 A1 | 12/2002 | Smith et al. | |
| 2003/0023201 A1 | 1/2003 | Lewis et al. | |
| 2003/0055442 A1 | 3/2003 | Laufer et al. | |
| 2003/0065359 A1 | 4/2003 | Weller et al. | |
| 2003/0093117 A1 | 5/2003 | Saadat | |
| 2003/0120289 A1 | 6/2003 | McGuckin, Jr. et al. | |
| 2003/0120292 A1 | 6/2003 | Park et al. | |
| 2003/0171760 A1 | 9/2003 | Gambale | |
| 2003/0187465 A1 | 10/2003 | Bailly et al. | |
| 2003/0191497 A1 | 10/2003 | Cope | |
| 2003/0216613 A1 | 11/2003 | Suzuki et al. | |
| 2003/0216754 A1 | 11/2003 | Kraemer et al. | |
| 2003/0220657 A1 | 11/2003 | Adams | |
| 2004/0044304 A1 | 3/2004 | Hill et al. | |
| 2004/0044364 A1 | 3/2004 | DeVries et al. | |
| 2004/0087976 A1 | 5/2004 | DeVries et al. | |
| 2004/0093024 A1 | 5/2004 | Lousararian et al. | |
| 2004/0116949 A1 | 6/2004 | Ewers et al. | |
| 2004/0133236 A1 | 7/2004 | Chanduszko | |
| 2004/0138529 A1 | 7/2004 | Wiltshire et al. | |
| 2004/0147958 A1 | 7/2004 | Lam et al. | |
| 2004/0148034 A1 | 7/2004 | Kagan et al. | |
| 2004/0153102 A1 | 8/2004 | Therin et al. | |
| 2004/0153103 A1 | 8/2004 | Schwartz et al. | |
| 2004/0162568 A1 | 8/2004 | Saadat et al. | |
| 2004/0215216 A1 | 10/2004 | Gannoe et al. | |
| 2004/0236357 A1 | 11/2004 | Kraemer et al. | |

(56) References Cited

U.S. PATENT DOCUMENTS

| | | |
|---|---|---|
| 2004/0243223 A1 | 12/2004 | Kraemer et al. |
| 2005/0004575 A1 | 1/2005 | Sgro et al. |
| 2005/0017781 A1 | 1/2005 | Honda |
| 2005/0043759 A1 | 2/2005 | Chanduszko |
| 2005/0075653 A1 | 4/2005 | Saadat et al. |
| 2005/0085829 A1 | 4/2005 | Kraemer et al. |
| 2005/0154405 A1 | 7/2005 | Kraemer et al. |
| 2005/0177176 A1 | 8/2005 | Gerbi et al. |
| 2005/0187565 A1 | 8/2005 | Baker et al. |
| 2005/0203547 A1 | 9/2005 | Weller et al. |
| 2005/0216040 A1 | 9/2005 | Gertner et al. |
| 2005/0228413 A1 | 10/2005 | Binmoeller et al. |
| 2005/0247320 A1 | 11/2005 | Stack et al. |
| 2005/0251176 A1 | 11/2005 | Swanstrom et al. |
| 2006/0009789 A1 | 1/2006 | Gambale |
| 2006/0190018 A1 | 8/2006 | Baker et al. |
| 2006/0253130 A1 | 11/2006 | Wolniewicz |
| 2006/0253142 A1 | 11/2006 | Bjerken |
| 2007/0021756 A1 | 1/2007 | Kortenbach |
| 2007/0021760 A1 | 1/2007 | Kelleher |
| 2007/0112363 A1 | 5/2007 | Adams |
| 2007/0129738 A1 | 6/2007 | Kraemer et al. |
| 2007/0191870 A1 | 8/2007 | Baker et al. |
| 2007/0191871 A1 | 8/2007 | Baker et al. |
| 2007/0219566 A1 | 9/2007 | Gambale |
| 2007/0276409 A1 | 11/2007 | Ortiz et al. |
| 2008/0015618 A1 | 1/2008 | Sonnenschein et al. |
| 2008/0287966 A1 | 11/2008 | Kraemer et al. |
| 2008/0294179 A1 | 11/2008 | Balbierz et al. |
| 2009/0177214 A1 | 7/2009 | Adams |
| 2009/0198254 A1 | 8/2009 | Laufer et al. |
| 2009/0236388 A1 | 9/2009 | Cole et al. |
| 2010/0241139 A1 | 9/2010 | Harshman |
| 2011/0196391 A1 | 8/2011 | Forsell |
| 2011/0213390 A1 | 9/2011 | Kraemer et al. |

FOREIGN PATENT DOCUMENTS

| | | |
|---|---|---|
| WO | 9960931 A1 | 12/1999 |
| WO | 0053102 A1 | 9/2000 |
| WO | 0078227 A1 | 12/2000 |
| WO | 0132084 A1 | 5/2001 |
| WO | 0135834 A1 | 5/2001 |
| WO | 0164964 A1 | 9/2001 |
| WO | 0167964 A2 | 9/2001 |
| WO | 0185034 A1 | 11/2001 |
| WO | 0189391 A1 | 11/2001 |
| WO | 0224058 A2 | 3/2002 |
| WO | 0224080 A2 | 3/2002 |
| WO | 0228289 A1 | 4/2002 |
| WO | 02082621 A1 | 10/2002 |
| WO | 02096327 A2 | 12/2002 |
| WO | 03061480 A1 | 7/2003 |
| WO | 03099140 A1 | 12/2003 |
| WO | 2004019787 A2 | 3/2004 |
| WO | 2004019788 A2 | 3/2004 |
| WO | 2004049982 A2 | 6/2004 |
| WO | 2004069055 A2 | 8/2004 |
| WO | 2005065412 A2 | 7/2005 |
| WO | 2005081817 A2 | 9/2005 |
| WO | 2006023764 A2 | 3/2006 |
| WO | 2006034484 A2 | 3/2006 |
| WO | 2006081368 A2 | 8/2006 |
| WO | 2007002817 A2 | 1/2007 |
| WO | 2007064713 A2 | 6/2007 |
| WO | 2010087756 A1 | 8/2010 |

OTHER PUBLICATIONS

Reappraisal of the flap valve mechanism in the gastroesophageal junction: A study of a new valvuloplasty procedure in cadavers; KjellB.A. Thor et al.; Acta Chir Scand 153:25-28, 1987; abstract.
The Plicator Procedure; 1 page; abstract, 1987.
Chuttani, MD. et al., "A novel endoscopic full-thickness plicator for treatment of GERD: an animal model study". Gastrointestinal Endoscopy, vol. 56, No. 1, 2002, pp. 116-122; abstract.
Jobe, et al., "Endoscopic Appraisal of the Gastroesophageal Valve After Antireflux Surgery", American Journal of Gastroenterology, ISSN 0002-9270; abstract, 2004.
International Search Report for PCT/US2012/054328, 2012.

\* cited by examiner

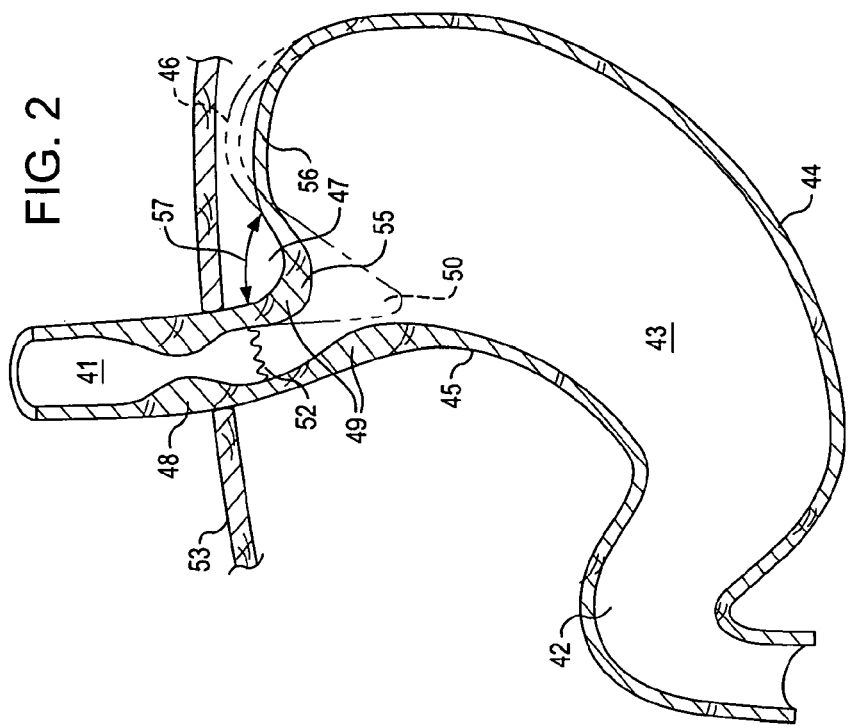
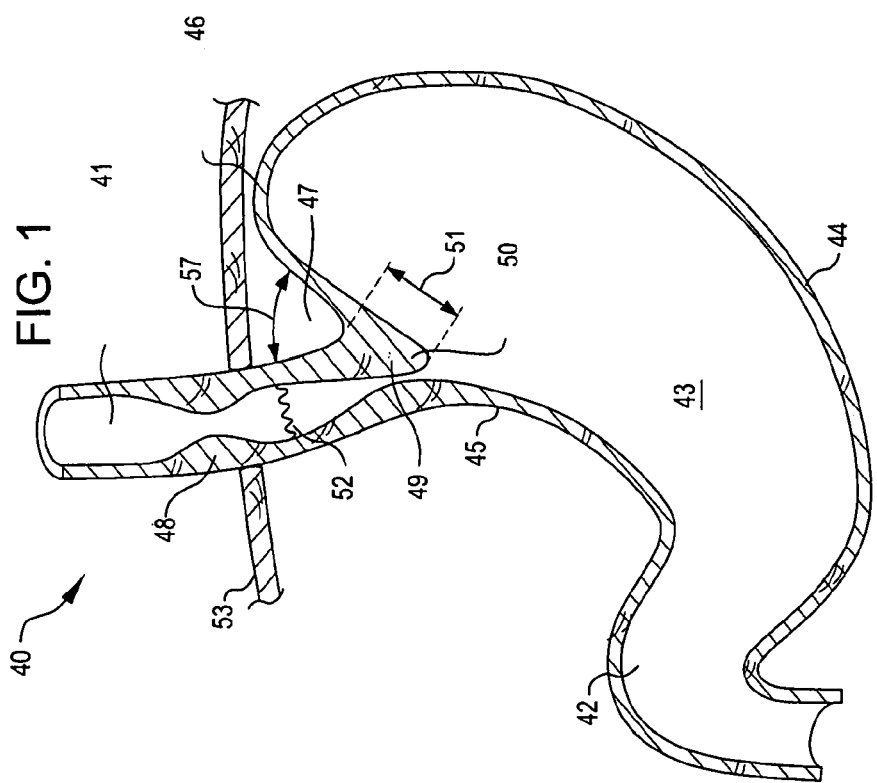

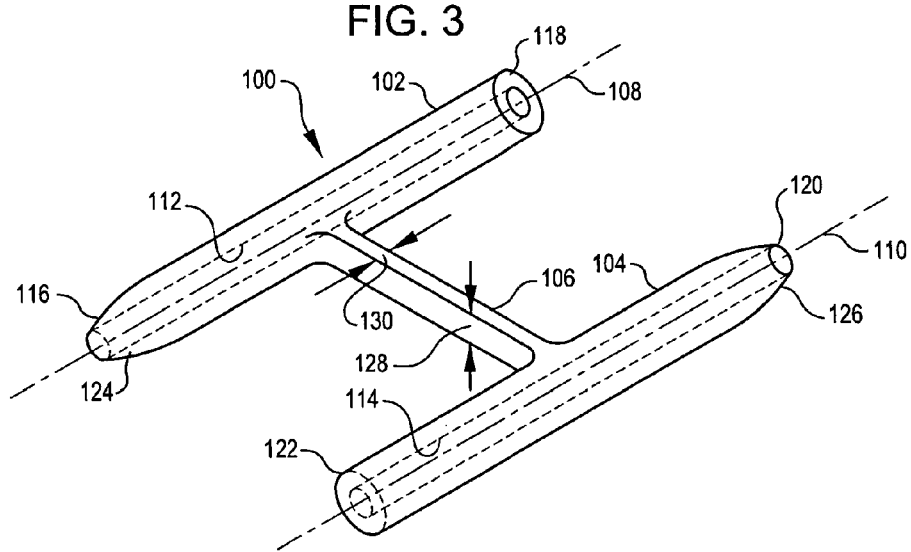
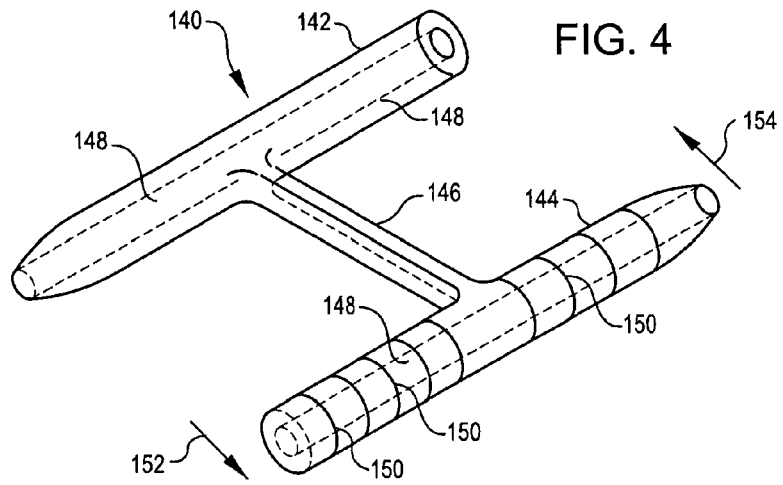

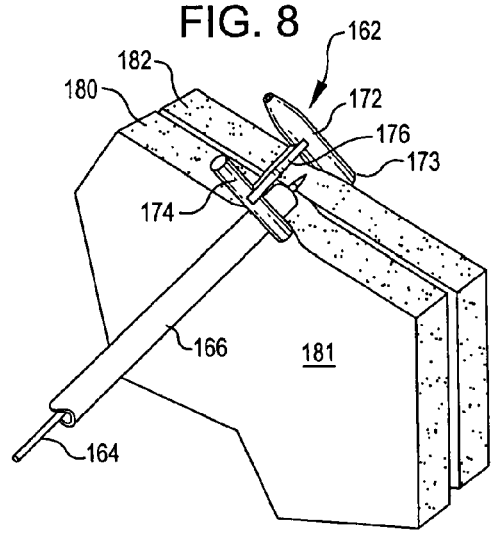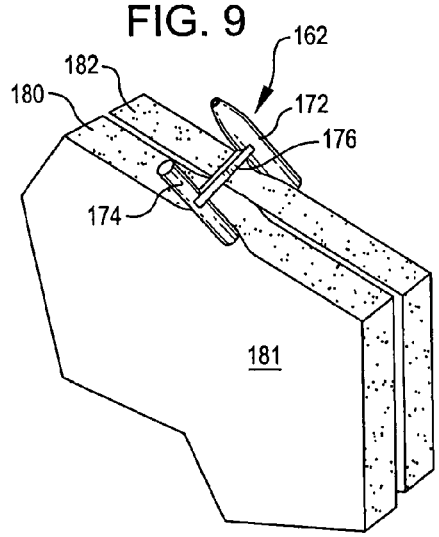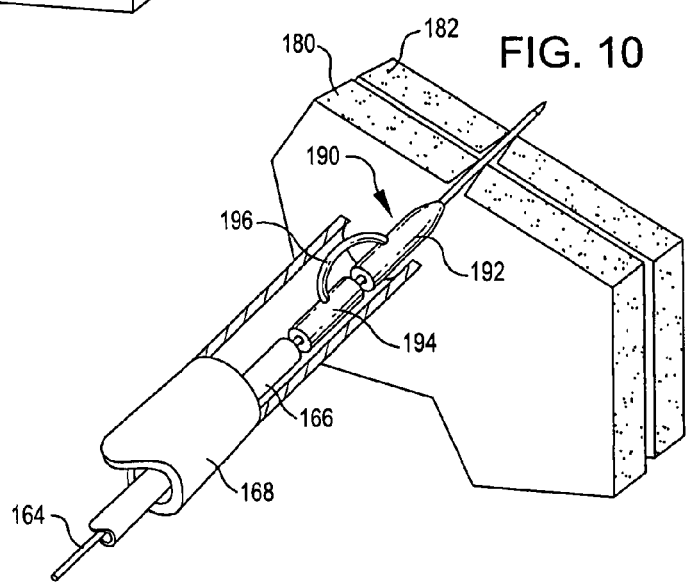

TISSUE FIXATION DEVICES AND ASSEMBLIES FOR DEPLOYING THE SAME

RELATED APPLICATION DATA

This application is a division of U.S. Ser. No. 12/590,203 filed Nov. 4, 2009, now U.S. Pat. No. 8,911,473, which is a continuation of U.S. Ser. No. 10/949,737 filed Sep. 23, 2004, now U.S. Pat. No. 7,623,287, which is a continuation-in-part application of U.S. Ser. No. 10/783,717 filed Feb. 20, 2004, now abandoned.

FIELD OF THE INVENTION

The present invention generally relates to tissue fixation devices, and more particularly to devices for treating gastroesophageal reflux disease using the same. The present invention more particularly relates to such tissue fixation devices which may be used in surgical environments and which are self-deploying.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-degree valve is created by a system of sutures. The Hill procedure restores the moveable flap, the cardiac notch and the Angle of His. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak. Involvement of esophageal tissue in the repair of a gastroesophageal flap valve poses unnecessary risks to the patient.

A new and improved apparatus and method for restoration of a gastroesophageal flap valve is fully disclosed in copending U.S. application Ser. No. 10/150,740, filed May 17, 2002, for TRANSORAL ENDOSCOPIC GASTROESOPHAGEAL FLAP VALVE RESTORATION DEVICE, ASSEMBLY, SYSTEM AND METHOD, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Whenever tissue is to be maintained in a shape as, for example, in the improved assembly last mentioned above, it is necessary to fasten at least two layers of tissue together. In applications such as gastroesophageal flap valve restoration, there is very limited room to maneuver a fastener deployment device. For example, this and other medical fastening applications provide confined working channels and spaces and often must be fed through an endoscope to permit visualization or other small lumen guide catheters to the place where the fasteners are to be deployed. To make matters worse, multiple fasteners may also be required. Hence, with current fasteners and deployment arrangements, it is often difficult to direct a single fastener to its intended location, let alone a number of such fasteners.

Once the fastening site is located, the fasteners employed must be truly able to securely maintain the tissue. Also, quite obviously, the fasteners are preferably deployable in the tissue in a manner which does not unduly traumatize the tissue.

SUMMARY

The present invention provides a fastener for use in a mammalian body, comprising a first member, a second member, the first and second members having first and second ends, and a connecting member fixed to each of the first and second members intermediate the first and second ends and extending between the first and second members. The first and second members are separated by the connecting member, and one of the first and second members has a longitudinal axis, a through channel along the axis arranged to be slidingly received on a tissue piercing deployment wire, and an elongated slot communicating with the through channel and dimensioned to receive the tissue piercing deployment wire.

The invention further provides a fastener assembly for use in a mammalian body, comprising a fastener including a first member, a second member, wherein the first and second members have first and second ends, and a connecting member fixed to each of the first and second members intermediate the first and second ends and extending between the first and second members, wherein the first and second members are separated by the connecting member, and wherein one of the first and second members has a longitudinal axis, a through channel along the axis, and an elongated slot communicating with the through channel. The assembly further comprises a deployment wire arranged to be slidingly received by the through channel and the elongated slot of the one of the first and second members and to pierce into the tissue, and a pusher that pushes the one of first and second members into the tissue while on the deployment wire.

The first member, second member, and the connecting member may all be formed of plastic material and in one piece.

The connecting member of the fastener may be formed of plastic elastic material. Alternatively, the connecting member may be formed of a plastic, permanently deformable material. The plastic material may include a color pigment contrasting with body tissue color to enable visualization of the fastener with an endoscope.

One end of the one of the first and second members of the fastener may further include a pointed tip. The pointed tip may comprise a truncated cone. Alternatively, the pointed tip may comprise a sectioned portion.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 1 is a front cross-sectional view of the esophageal-gastro-intestinal tract from a lower portion of the esophagus to the duodenum;

FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines);

FIG. 3 is a perspective view of a fastener embodiment;

FIG. 4 is a perspective view of another fastener embodiment;

FIG. 8 is a perspective view of the assembly of FIG. 5 shown with the fastener initially deployed;

FIG. 9 is a perspective view showing the fastener of the assembly of FIG. 5 fully deployed and securely fastening a pair of tissue layers together;

FIG. 10 is a perspective view with portions cut away of another fastener deployment assembly embodiment in an early stage of deploying another fastener embodiment;

DETAILED DESCRIPTION

Figure 5:
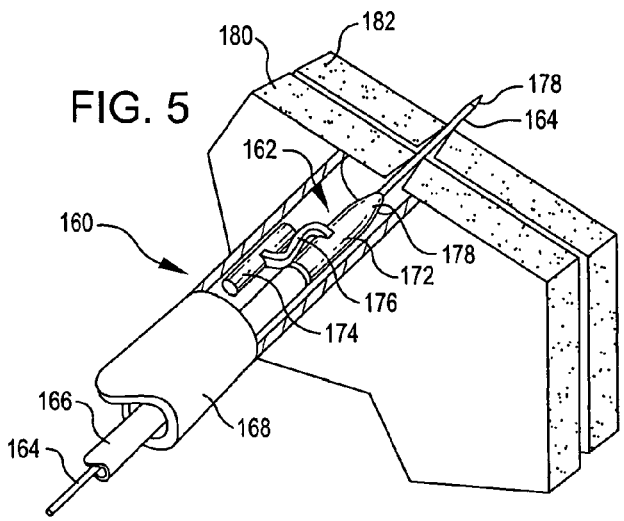
FIG. 5 is a perspective view with portions cut away of a fastener assembly embodiment in an early stage of deploying a fastener embodiment.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., The gastroesophageal flap valve: in vitro and in vivo observations, Gastrointestinal Endoscopy 1996:44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently is a device for restoring the normal gastroesophageal flap valve anatomy, which device is one embodiment of the present invention.

Referring now to FIG. 3, it is a perspective view of a fastener embodiment 100. The fastener 100 generally includes a first member 102, a second member 104, and a connecting member 106. As may be noted in FIG. 3, the first member 102 and second member 104 are substantially parallel and substantially perpendicular to the connecting member 106 which connects the first member 102 to the second member 104.

The first and second members 102 and 104 are generally cylindrical. Each has a longitudinal axis 108 and 110 and a through channel 112 and 114 along the longitudinal axes 108 and 110. The through channels 112 and 114 are formed by through bores which are dimensioned to be slidingly received on a tissue piercing deployment wire to be described hereinafter.

The first member 102 also includes a first end 116 and a second end 118. Similarly, the second member 114 includes a first end 120 and a second end 122. The first ends 116 and 120 form pointed dilation tips 124 and 126, respectively. The dilation tips 124 and 126 are conical and more particularly take the shape of truncated cones. The pointed tips 129 and 126 are pointed in opposite directions.

The first and second members 102 and 104 and the connecting 106 may be formed of different materials and have different textures. These materials may include, for example, plastic materials such as polypropylene, polyethylene, polyglvcolic acid, polyurethane, or a thermoplastic elastomer. Alternatively, the fastener may be formed of a metal, such as stainless steel or a shape memory metal, such as Nitinol. As may be further noted in FIG. 3, the connecting member 106 has a vertical dimension 128 and a horizontal dimension 130 which is transverse to the vertical dimension. The horizontal dimension is substantially less than the vertical dimension to render the connecting member 106 readily bendable in a horizontal plane. The connecting member is further rendered bendable by the nature of the plastic material from which the fastener 100 is formed. The connecting member may be formed from either an elastic plastic or a permanently deformable plastic. An elastic material would prevent compression necrosis in some applications.

Referring now to FIG. 4, it illustrates another fastener embodiment 140. As with the fastener 100 of FIG. 3, the fastener 140 includes a first member 142, a second member 144, and a connecting member 146. The fastener 140 may be formed in one piece and from plastic material similar to the fastener 100 of FIG. 3. The fasteners 100 and 140 may be formed of a plastic material which includes a color pigment, for example pthalocyanine blue, for contrasting with the color of body tissue to enable visualization of the fastener with an endoscope during the deployment of the fasteners. In addition, as may be seen in FIG. 4, the fastener 140 is impregnated with radio opaque material 148 so as to render the fastener 140 at least partially viewable under fluoroscopy. The radio opaque particles may be, for example, barium sulfate, bismuth subcarbonate, tungsten powder or tantalum powder.

In addition to the foregoing, the second member 144 of the fastener 140 includes a plurality of longitudinally spaced vertical slots 150. This renders the second member 144 flexible in a direction opposite the slots but stiff in a direction of the slots. Hence, the second member 144 is resistant to bending in a first direction indicated by arrow 152 while being substantially less resistant to bending in a direction indicated by arrow 154. The reduced resistance to bending in the direction 154 of the second member 144 of the fastener 140 may be utilized to advantage in the deployment of the fastener 140.

Referring now to FIG. 5, it is a perspective view with portions cut away of a fastener assembly embodiment 160. The tissue layer portions above the fastener 162 have been shown cut away in FIGS. 5-9 to enable the deployment procedure to be seen more clearly. The assembly 160 generally includes a fastener 162, a deployment wire 164, a pusher 166, and a guide tube 168.

The fastener 162 takes the form of a further fastener embodiment and includes a first member 172, a second member 174, and a connecting member 176. The fastener 162 differs from the fasteners 100 and 140 of FIGS. 3 and 4, respectively, in that the second member 174 is of solid construction and does not include a longitudinal through channel or a pointed tip. However, the first member 172 includes a through channel as previously described and a pointed tip 178.

The first member 172 of the fastener 162 is slidingly received on the deployment wire 164. The deployment wire 164 has a pointed tip 178 for piercing the tissue layers 180 and 182 to be fastened together. As will be seen hereinafter, and in accordance with further aspects of the present invention, the tissue layers 180 and 182 may be folded stomach tissue which are to be fastened and maintained together to form and maintain a gastroesophageal flap valve.

As will be noted in FIG. 5, the tissue piercing wire 164, fastener 162, and the pusher 166 are all within the guide tube 168. The guide tube 168 may take the form of a catheter, for example.

As will be further noted in FIG. 5, the second member 174 is disposed along side the first member 172. This is rendered possible by the flexibility of the connecting member 176. Preferably, the first member, connecting member, and second member are arranged so that the connecting member 176 lies to the side of the first member 172 and the second member 174.

With the first member 172 of the fastener 162 slidingly received on the tissue piercing wire 164 and with the pusher 166 just touching the first member 172 on the tissue piercing wire 164, the tip 178 of the tissue piercing wire 164 pierces the tissue layers 180 and 182. The subassembly of the tissue piercing wire 164, fastener 162, and pusher 166 may be guided to its intended location relative to the tissue layers 180 and 182 by the guide tube 168. As will be seen hereinafter, this subassembly may be alternatively guided by guide channels arranged to accommodate the tissue piercing wire 164, fastener 162, pusher 166, and the guide tube 168.

Figure 6:
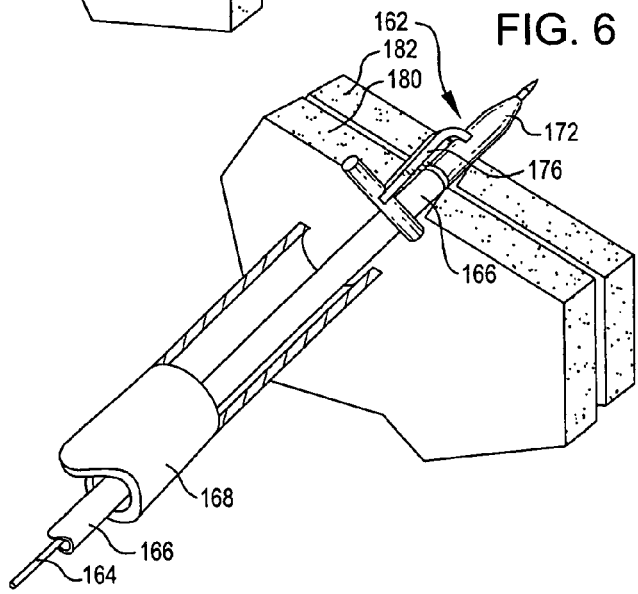
FIG. 6 is a perspective view of the assembly of FIG. 5 shown with the fastener being driven in the tissue layers to be fastened.
Figure 7:
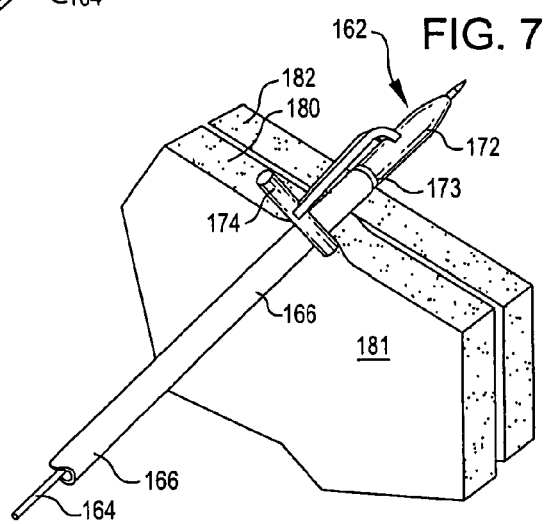
FIG. 7 is a perspective view of the assembly of FIG. 5 shown with the fastener extending through the tissue layers to be fastened.

Once the tissue piercing wire 164 has pierced the tissue layers 180 and 182 to be fastened together, the pusher 166 may be utilized to push the first member 172 of the fastener 162 through the tissue layers 180 and 182 on the tissue piercing wire 164. This is illustrated in FIG. 6. As the pusher 166 pushes the first member 172 through the tissue layers 180 and 182, the connecting member 176 follows along beside and immediately adjacent to the first member 172 of the fastener 162 and the pusher 166. As may be seen in FIG. 7, the pusher 166 continues to push the first member 172 of the fastener 162 through the tissue layers 180 and 182 on the tissue piercing wire 164 until the end 173 of the first member 172 engaging the pusher 166 clears the second tissue layer 182. It may also be noted that at this time, the second member 174 of the fastener 162 has engaged the surface 181 of tissue layer 180.

Referring now to FIG. 8, it will be seen that once the end 173 of the first member 172 has cleared the tissue layer 182, the tissue piercing wire 164 is then retracted within the pusher 166 to release the first member 172. The first member 172 being thus released from the tissue piercing wire 164 will return to its original configuration substantially parallel to the second member 174 and substantially perpendicular to the connecting member 176. When the first member 172 is deployed as shown in FIG. 8, the tissue piercing wire 164 and pusher 166 may be withdrawn.

FIG. 9 illustrates the fastener 162 in its deployed position. It will be noted that the tissue layers 180 and 182 are fastened together between the first member 172 of the fastener 162 and the second member 174 of the fastener 162. The connecting member 176 extends through the tissue layers 180 and 182.

FIG. 10 is a perspective view with portions cut away of another fastener and fastener assembly embodiment. The fastener 190 of FIG. 10 includes a first member 192, a second member 194, and a connecting member 196. The fastener 190 is similar to the fastener 100 of FIG. 3 in that both the first member 192 and second member 194 includes a through bore. This permits the first member 192 and second member 194 to be slidingly received in line with each other on the tissue piercing wire 164. With both the first member 192 and second member 194 being disposed on the tissue piercing wire 164, the second member 194 will not be deployed until after the tissue piercing wire 164 is retracted from the second member 194. As a result, the second member of the fastener 162 illustrated in FIGS. 5-9 will deploy before the second member 194 of fastener 190. However, the arrangement illustrated in FIG. 10 may be advantageous where space is at a premium and the guide tube 168 has a reduced diameter. The deployment of the fastener 190 by the tissue piercing wire 164, the pusher 166, and the guide tube 168 is otherwise similar to the deployment procedure described above with respect to FIGS. 5-9.

Figure 11:
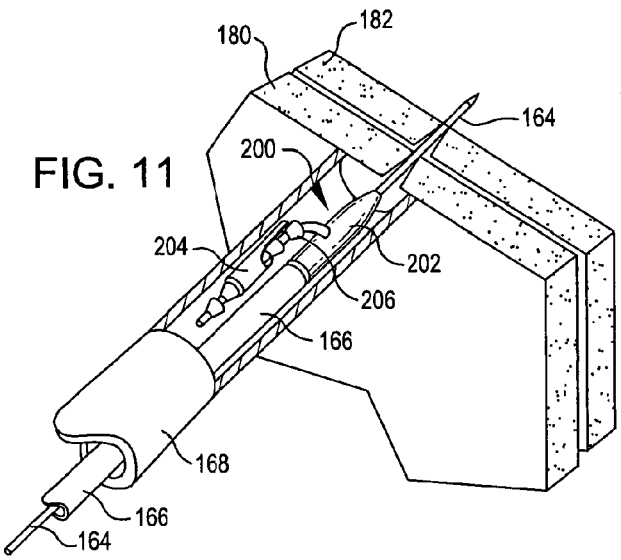
FIG. 11 is a perspective view with portions cut away of another fastener deployment assembly embodiment in an early stage of deploying another fastener embodiment.
Figure 12:
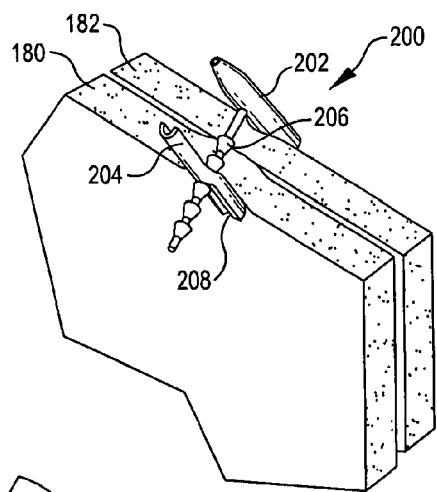
FIG. 12 is a perspective view showing the fastener of the assembly of FIG. 11 fully deployed and securely fastening a pair of tissue layers together.

FIG. 11 shows another fastener embodiment 200. The fastener 200 is illustrated in an initial stage of deployment by the tissue piercing deployment wire 164, the pusher 166, and the guide tube 168 to fasten tissue layers 180 and 182 together. FIG. 12 shows the fastener 200 after deployment fastening tissue layers 180 and 182 together. The fastener 200 may be deployed as previously described in connection with FIGS. 5-9.

The fastener 200 includes a first member 202, a second member 204, and a connecting member 206. The connecting member 206 takes the form of a beaded chain and the second member is bifurcated at 208 to permit the second member 204 to be positioned between any pair of beads of the connecting member 204. This renders the length of the connecting member 206 between the first and second members 202 and 204 adjustable to accommodate tissue layers of various densities and thicknesses.

Figure 13:
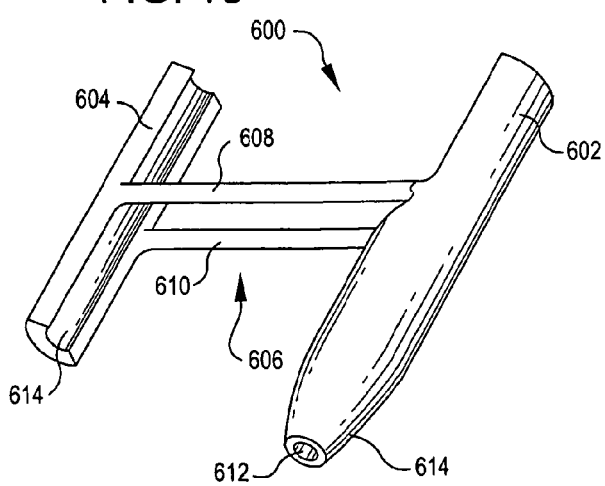
FIG. 13 is a perspective view of another fastener embodiment.
Figure 14:
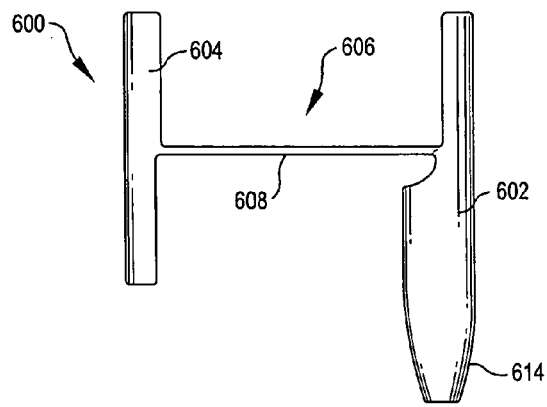
FIG. 14 is a top plan view of the fastener of FIG. 13.

Referring now to FIGS. 13 and 14, they illustrate still another fastener 600. The fastener 600 generally includes a first member 602, a second member 604, and a connecting member structure 606. As may be noted in FIGS. 13 and 14 the connecting member structure includes a plurality of connecting members 608 and 610. The connecting members 608 and 610 connect the first member 602 to the second member 604.

The first member 602 is cylindrical and the second member 604 is a cylindrical half-section. Each has a longitudinal through channel 612 and 614. The through channel 614 is a through bore which is dimensioned to be a slidingly received on a tissue piercing deployment wire. The channel 614 is dimensioned to be optionally carried on the deployment wire prior to deployment. The first member 602 also includes a conical pointed tip 614.

The fastener 600 may be formed of any of the plastic or metal materials previously described. As may be further noted in FIGS. 13 and 14 the connecting members 600 and 610 are relatively thin to render the connecting member structure 606 readily bendable for ease of deployment. The connecting member structure is further rendered bendable of course by the nature of the plastic or metal material from which the fastener 600 is formed.

Figure 15:
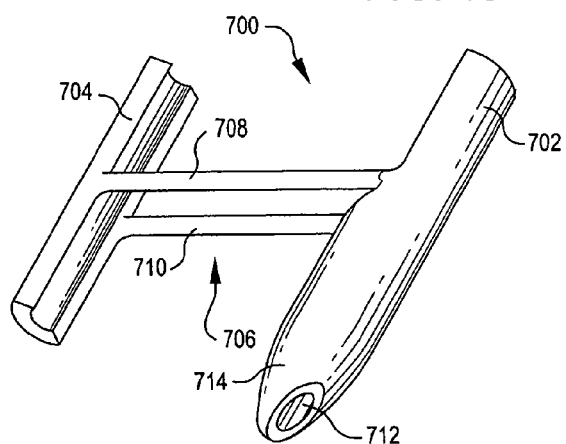
FIG. 15 is a perspective view of still another fastener embodiment.
Figure 16:
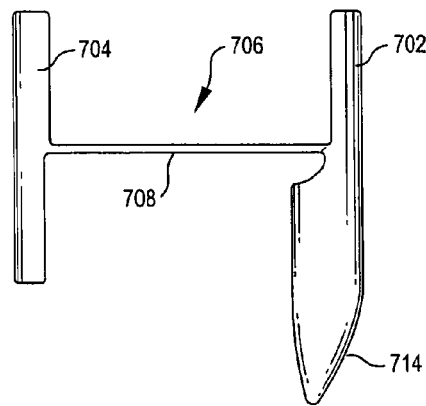
FIG. 16 is a top plan view of the fastener of FIG. 15.

Referring now to FIGS. 15 and 16, they illustrate another fastener embodiment 700. As with the previous fastener, the fastener 700 includes a cylindrical first member 702, cylindrical half-section 704 and a connecting member structure 706. The connecting member structure 706 includes connecting members 708 and 710. Here however, the pointed tip 714 takes the form of a tapered section of the first member 702.

As in the previous embodiment the first member 702 of the fastener 700 may be slidingly received on a deployment wire. The deployment wire may be received by a bore 712. The fasteners 600 and 700 may be deployed as previously described.

Figure 17:
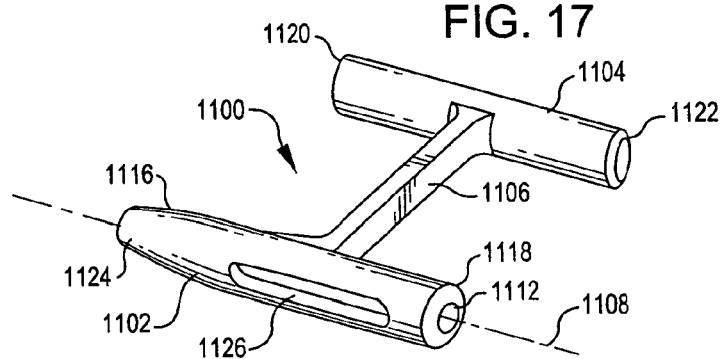
FIG. 17 is a perspective view of a fastener according to an embodiment of the invention.

Referring now to FIG. 17, it is a perspective view of a fastener 1100 according to an embodiment of the invention. The fastener 1100 generally includes a first member 1102, a second member 1104, and a connecting member 1106. As may be noted in FIG. 17, the first member 1102 and second member 1104 are substantially parallel and substantially perpendicular to the connecting member 1106 which connects the first member 1102 to the second member 1104.

The first member 1102 is generally cylindrical. It has a longitudinal axis 1108 and a through channel 1112 along the longitudinal axes 1108. The through channel 1112 is formed by a through bore which is dimensioned to be slidingly received on a tissue piercing deployment wire as previously described.

The first member 1102 also includes a first end 1116 and a second end 1118. Similarly, the second member 1104 includes a first end 1120 and a second end 1122. The first end 1116 of member 1102 forms a pointed dilation tip 1124. The dilation tip 1124 is conical and more particularly takes the shape of a truncated cone.

The first and second members 102 and 104 and the connecting 106 may be formed of the various materials previously described. As may be further noted in FIG. 17, the connecting member 1106 has a horizontal dimension that is substantially less than its vertical dimension to render the connecting member 1106 readily bendable in a horizontal plane. The connecting member is further rendered bendable by the nature of the plastic material from which the fastener 1100 may be formed.

Figure 18:
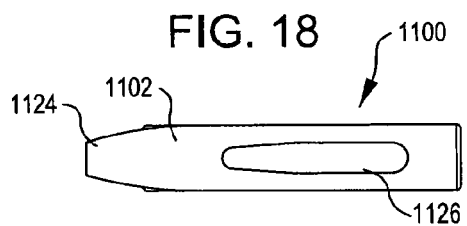
FIG. 18 is a side view of the fastener of FIG. 17.

FIG. 18 illustrates a side view of the fastener 1100. Here, it will be noted that the 1102 including an elongated slot 1126. The slot 1126 has a transverse dimension for receiving the tissue piercing deployment wire during deployment of the fastener 1100. As will be seen subsequently, this permits early deployment of the first member 1102 and decreases compression on the tissue layers. The elongated slot 1126 extends substantially parallel to the through channel 1112 and the center axis 1108 of the first member 1102.

Figure 19:
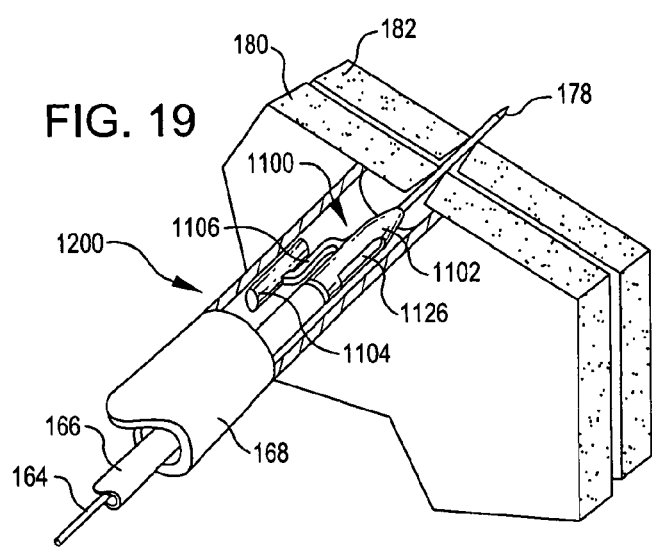
FIG. 19 is a perspective view with portions cut away of a fastener assembly according to an embodiment of the invention in an early stage of deploying the fastener of FIG. 17.

Referring now to FIG. 19, it is a perspective view with portions cut away of a fastener assembly 1200 embodying the present invention for deploying the fastener 1100. The tissue layer portions above the fastener 1100 have been shown cut away in FIGS. 19-22 to enable the deployment procedure to be seen more clearly. The assembly 1200 generally includes the fastener 1100, the deployment wire 164, the pusher 166, and the guide tube 168.

The first member 1102 of the fastener 1100 is slidingly received on the deployment wire 164. The deployment wire 164 has a pointed tip 178 for piercing the tissue layers 180 and 182 to be fastened together. The tissue piercing wire 164, fastener 1100, and the pusher 166 are all within the guide tube 168. The guide tube 168 may take the form of a catheter, for example, as previously mentioned.

As will be further noted in FIG. 19, the second member 1104 is disposed along side the first member 1102. This is rendered possible by the flexibility of the connecting member 1106.

With the first member 1102 of the fastener 1100 slidingly received on the tissue piercing wire 164 and with the pusher 166 just touching the first member 1102 on the tissue piercing wire 164, the tip 178 of the tissue piercing wire 164 pierces the tissue layers 180 and 182. The subassembly of the tissue piercing wire 164, fastener 1100, and pusher 166 may be guided to its intended location relative to the tissue layers 180 and 182 by the guide tube 168.

Figure 20:
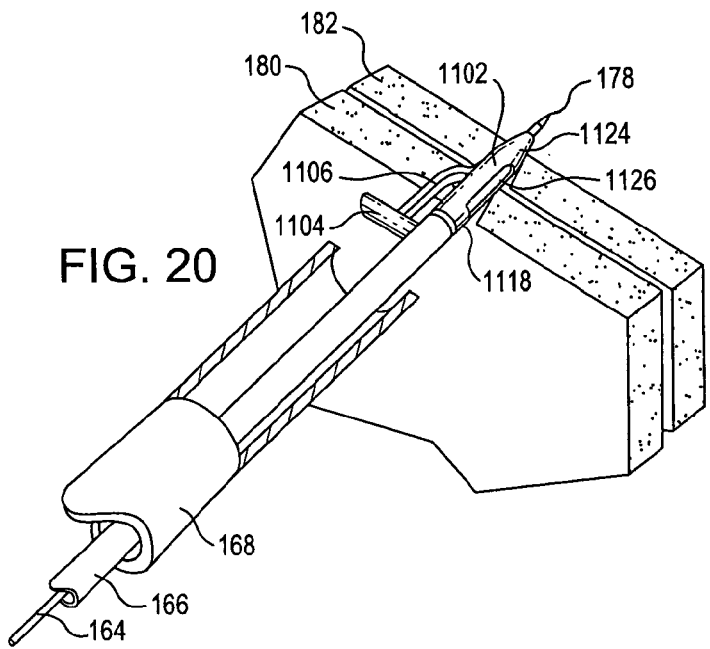
FIG. 20 is a perspective view of the assembly of FIG. 19 shown with the fastener being driven in the tissue layers to be fastened.

Once the tissue piercing wire 164 has pierced the tissue layers 180 and 182 to be fastened together, the pusher 166 may be utilized to push the first member 1102 of the fastener 1100 through the tissue layers 180 and 182 on the tissue piercing wire 164. This is illustrated in FIG. 20. As the pusher 166 pushes the first member 1102 through the tissue layers 180 and 182, the connecting member 1106 follows along beside and immediately adjacent to the first member 1102 of the fastener 1100 and the pusher 166.

Figure 21:
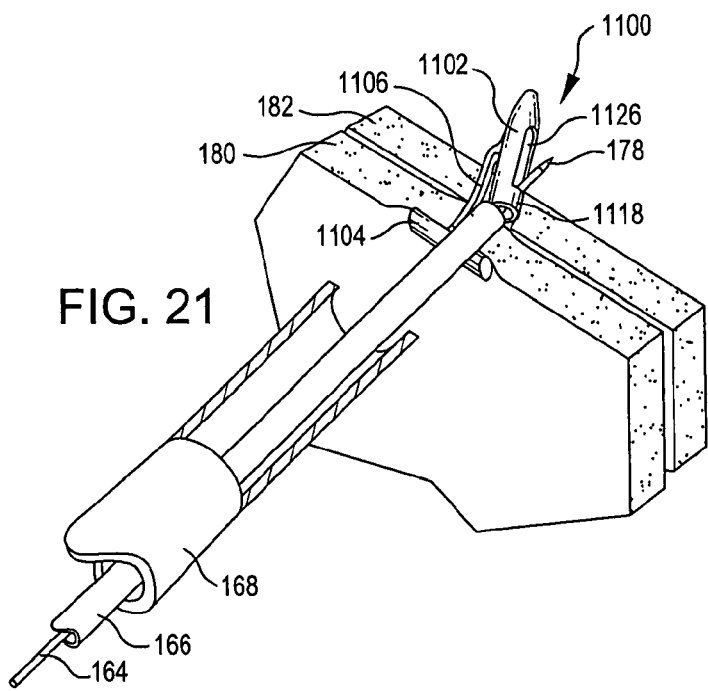
FIG. 21 is a perspective view of the assembly of FIG. 19 shown with the fastener extending through the tissue layers to be fastened and early partial fastener deployment according to the invention.

As may be seen in FIG. 21, when the second member engages tissue layer 180, the pusher 166 may be retracked within the first member 1102 of the fastener 1100. The tissue piercing wire 164 is received within the elongated slot 1126 to permit the tissue piercing wire 164 to release the first member 1102 for early deployment. The second end 1118 of the first member 1102 now clears the second tissue layer 182. This early release of the first member 1102 reduces the compression on the tissue layers 180 and 182 even though the second member 1104 has engaged the tissue layer 180.

Figure 22:
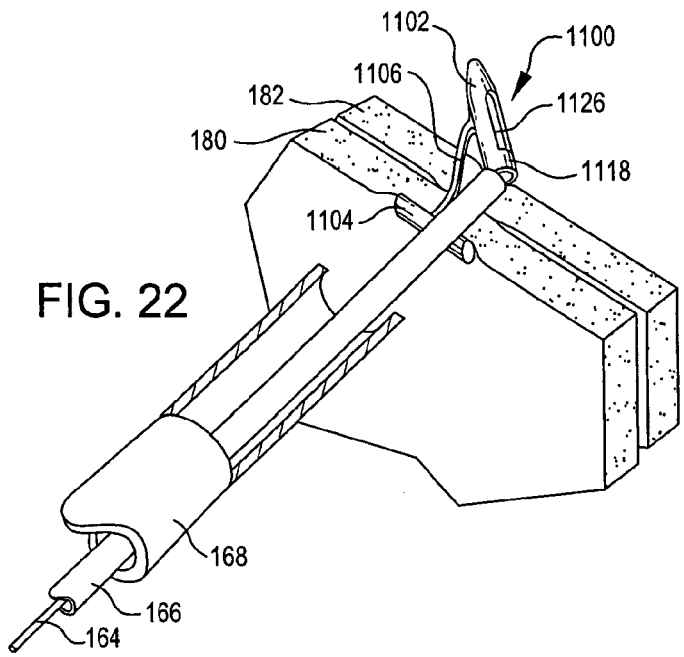
FIG. 22 is a perspective view of the assembly of FIG. 19 shown with the fastener initially deployed.

Referring now to FIG. 22, it will be seen that once the second end 1118 of the first member 1102 has cleared the tissue layer 182, the tissue piercing wire 164 is then retracted into the pusher 166 to fully release the first member 1102. The first member 1102 being thus fully released from the tissue piercing wire 164 will return to its original configuration substantially parallel to the second member 1104 and substantially perpendicular to the connecting member 1106. When the first member 1102 is deployed as shown in FIG. 22, the tissue piercing wire 164 and pusher 166 may be withdrawn.

Figure 23:
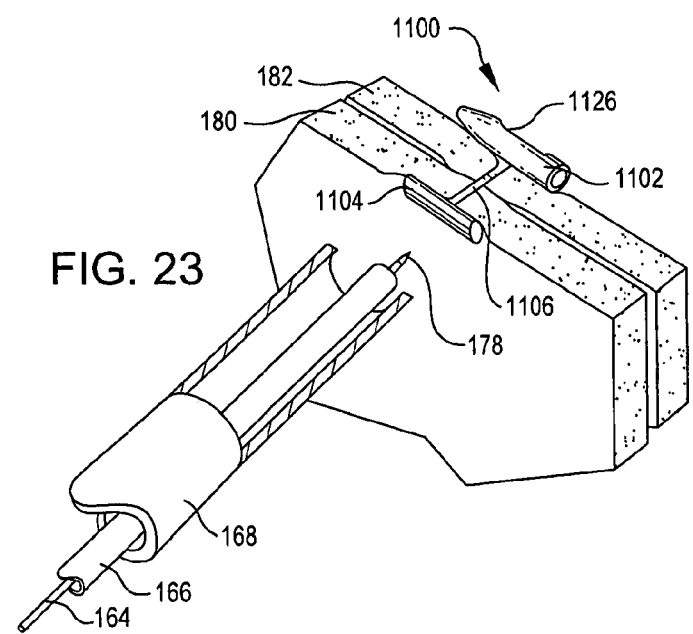
FIG. 23 is a perspective view showing the fastener of the assembly of FIG. 19 fully deployed and securely fastening a pair of tissue layers together.

FIG. 23 illustrates the fastener 1100 in its fully deployed position. It will be noted that the tissue layers 180 and 182 are fastened together between the first member 1102 of the fastener 1100 and the second member 1104 of the fastener 1100. The connecting member 1106 extends through the tissue layers 180 and 182.

While particular embodiments of the present invention have been shown and described, modifications may be made, and it is therefore intended in the appended claims to cover all such changes and modifications which fall within the true spirit and scope of the invention.

What is claimed is:

1. A fastener for use in a mammalian body, comprising:
a first member;
a second member,
both the first and second members having first and second ends; and
a connecting member fixed to each of the first and second members intermediate the first and second ends and extending between the first and second members,
the first and second members being separated by the connecting member, and
one of the first and second members having a longitudinal axis, a through channel along the axis arranged to be slidingly received on a tissue piercing deployment wire, and an elongated slot which is substantially parallel to the through channel and communicating with the through channel and dimensioned to receive the tissue piercing deployment wire.

2. The fastener of claim 1 wherein the connecting member is flexible and permits another one of the first and second members to be next to the one of the first and second members when the one of the first and second members is on the tissue piercing deployment wire.

3. The fastener of claim 1 wherein one end of the one of the first and second members further includes a pointed tip.

4. The fastener of claim 3 wherein the pointed tip is conical.

5. The fastener of claim 3 wherein the pointed tip comprises a sectioned portion.

6. The fastener of claim 1 wherein the through channel comprises a through bore.

7. The fastener of claim 1 wherein the connecting member is formed of elastic material.

8. The fastener of claim 1 wherein the first member, the second member, and the connecting member are all formed of plastic material.

9. The fastener of claim 8 wherein the first member, the second member, and the connecting member are all formed in one piece.

10. The fastener of claim 8 wherein the connecting member is formed of plastic elastic material.

11. The fastener of claim 8 wherein the connecting member is formed of a plastic, permanently deformable material.

12. The fastener of claim 8 wherein the plastic material includes a color pigment contrasting with body tissue color to enable visualization of the fastener with an endoscope.

13. The fastener of claim 1 wherein the first and second members and the connecting member are formed of different materials.

14. The fastener of claim 1 wherein the fastener is formed of metal.

15. The fastener of claim 14 wherein the metal is a shape memory material.

16. The fastener of claim 15 wherein the metal is Nitinol.

* * * * *